United States Patent
Yamamoto et al.

(10) Patent No.: US 6,350,477 B1
(45) Date of Patent: Feb. 26, 2002

(54) FOOD MATERIAL CONTAINING ANTIOXIDANT INGREDIENT DERIVED FROM CITRUS FRUITS

(75) Inventors: Kanefumi Yamamoto; Hiroaki Mieda; Masanori Hiramitsu; Yoshiaki Miyake, all of Aichi-ken (JP)

(73) Assignee: Pokka Corporation (JP)

( * ) Notice: Subject to any disclaimer, the term of this patent is extended or adjusted under 35 U.S.C. 154(b) by 0 days.

(21) Appl. No.: 09/421,934

(22) Filed: Oct. 21, 1999

(30) Foreign Application Priority Data

Nov. 27, 1998 (JP) ............................................. 10-352197
Jun. 9, 1999 (JP) ............................................. 11-162207

(51) Int. Cl.$^7$ ..................... A61K 35/78; A61K 31/35; A01N 43/16

(52) U.S. Cl. ..................... 424/736; 514/449; 514/451; 514/454; 514/455; 426/425; 426/429; 426/431; 426/481; 426/489; 426/495; 426/599

(58) Field of Search ................ 424/195.1, 736; 514/449, 451, 454, 455; 426/425, 429, 431, 481, 489, 495, 599

(56) References Cited

FOREIGN PATENT DOCUMENTS

| JP | 08073337 | * | 3/1996 |
| JP | 9-48969 | | 2/1997 |
| JP | 09048969 | * | 2/1997 |

OTHER PUBLICATIONS

Miyake et al. Food Sci. Technol. Int., Tokyo. vol. 3 (1), pp. 84–89, 1997.*
Bocco et al. J. Agric. Food Chem. vol. 46 (6), pp. 2123–2129, abstract enclosed, 1998.*
Nogata et al. J. Chromatogr. vol. 667 (1–2), pp. 59–66, abstract enclosed, 1994.*
Patent Abstract for KR 9411917, Dec. 27, 1994
Patent Abstract for KR 9402797, Apr. 2, 1994.

* cited by examiner

Primary Examiner—Christopher R. Tate
(74) Attorney, Agent, or Firm—Burns, Doane, Swecker, & Mathis, L.L.P.

(57) ABSTRACT

A process for producing a food material having a high concentration of eriocitrin, which comprises extracting a juice, a peel and a squeezed juice refuse of a citrus fruit with a polar solvent, applying the extract to a synthetic adsorption resin, and separating and recovering the food material having the high concentration of eriocitrin using an organic solvent such as hydrous alcohol. A food material having a high concentration eriocitrin as an antioxidant ingredient can industrially be produced quite efficiently without entraining an ingredient of a bitter taste, and drink and food having a high antioxidant effect can be produced.

13 Claims, No Drawings

FOOD MATERIAL CONTAINING ANTIOXIDANT INGREDIENT DERIVED FROM CITRUS FRUITS

DETAILED DESCRIPTION OF THE INVENTION

1. Field of the Invention

The present invention relates to production of a food material having a high concentration of eriocitrin that is an antioxidant ingredient derived from citrus fruits, and use thereof. The invention is to produce a food material having a high concentration of eriocitrin from a flesh, a juice, a peel or a squeezed residue of lemon or lime having a high concentration of eriocitrin, an antioxidant ingredient of citrus fruits, and to use the same as a beverage or a food having a high antioxidant effect by adding the same to a beverage or a food.

Especially, a peel and a squeezed residue which can be used in the invention are secondary products given when squeezing a fruit juice, and the peel after having been squeezed is a portion which is discharged and mostly discarded along with a large amount of water. The extraction of an active ingredient by reusing this portion is industrially quite an effective invention, and this is extremely useful from the standpoint of reuse of a waste.

2. Description of the Related Art

Eriocitrin has a structural name, eriodictyol-7-rutinoside, and it is a flavonoid glycoside in which rutinose (disaccharide: glucose and rhamnose) is bound to eriodictyol belonging to a flavanone of flavonoid compounds. Eriocitrin is present in citrus fruits, and especially contained in lemon and lime in a large amount. It is also present in oranges. However, it has been totally unknown that eriocitrin has an excellent antioxidant property. This is a new knowledge that the present inventors found before for the first time. A novel invention on an antioxidant material derived from citrus fruits based on this new knowledge was already filed as Japanese Patent Application No. 7-218286 (JP-A-9-48969).

PROBLEMS SOLVED BY THE INVENTION

In Japanese Patent Application No. 7-218286 (JP-A-9-48969) of the present applicant, for producing eriocitrin, a citrus fruit is first extracted with water, an organic solvent or a mixture thereof. The extraction is conducted at from room temperature to elevated temperature. Then, the extract is concentrated (under reduced pressure), treated with a resin, and purified through high-performance liquid chromatography or another chromatography. An active fraction is collected, and dried through freeze-drying to obtain a purified powder of eriocitrin. This method is acceptable at a laboratory level, but the purification step is intricate and time-consuming. The resulting eriocitrin powder is quite expensive. Accordingly, when eriocitrin obtained by this method is used as drink and food, the drink and food are naturally expensive. In case of the drink and food, the high cost of the product is undesirable, and the low cost thereof is required. In this respect, the conventional technique is still unsatisfactory.

The invention aims to industrially produce a less costly food material having a high concentration of eriocitrin.

MEANS FOR SOLVING THE PROBLEMS

It has been found that in the step of removing an unnecessary peel along with feeding water after squeezing a juice of lemon or lime, the feeding water has a high concentration of eriocitrin. On the basis of this finding, researches have been assiduously conducted investigations to solve the problems, and a process for obtaining a food material having a high concentration of eriocitrin has been worked out upon focusing on the facts that eriocitrin is present in a peel in a large amount and that eriocitrin has quite a high water solubility.

When the production is conducted using feeding water of the peel as stated above, a material having a high concentration of eriocitrin can be obtained by concentrating this feeding water, namely, the water extract of the peel. However, since the resulting product has quite bitter and rough tastes, it cannot be used in a wide variety of beverages and foods as a food material.

In order to remove the bitter and rough tastes, the water extract was subjected to treatment with a synthetic adsorption resin. Then, eriocitrin was also adsorbed thereon. This treatment is not problematic when it aims to remove the bitter and rough tastes as in the conventional technique. However, a new technical problem cannot be achieved that a food material having a high concentration of eriocitrin and free from bitter and rough tastes is obtained as in the invention. Even when a synthetic adsorption resin is treated with an organic solvent, adsorption substances are all recovered, meaning that ingredients of bitter and rough tastes are also recovered in addition to eriocitrin. Consequently, the resulting material cannot be applied to drink and food products in view of the taste.

Therefore, an extract obtained by extracting a peel, a juice and a squeezed residue of citrus fruits containing eriocitrin with a polar solvent was applied to a synthetic adsorption resin to adsorb eriocitrin thereon, and it was recovered using hydrous ethanol. Then, it was found that a food material having a high concentration of eriocitrin could industrially be obtained at a low cost upon selectively removing ingredients of bitter and rough tastes. That is, it has been identified for the first time that an eluent (organic solvent) for recovering an adsorption product is selected and a specific organic solvent is used, whereby only eriocitrin can selectively be recovered, and that it can selectively be recovered industrially through quite a simple operation. As a result of further investigations based on these useful new findings, the invention has been finally completed.

The invention is described in detail below.

In practicing the invention, at least one of a peel and a squeezed juice residue which are secondary products provided after obtaining a juice and a squeezed juice of citrus fruits such as lemon, lime and the like is first extracted with a polar solvent.

Examples of the citrus fruits include lemon, lime, grapefruit, "yuzu" (Citrus junos), navel orange, Valencia orange, sour orange, "hassaku" (Citrus hassaku), Satsuma mandarin, "iyokan" (Citrus iyo), "daidai" (Citrus aurantium), Kabosu and Ponkan mandarin. These can be used singly or in combination. Lemon and lime are preferably used because these have a high concentration of eriocitrin.

The fruit juice thereof can be obtained by the Brown squeezing method or the FMC squeezing method. It is advisable that secondary products obtained by squeezing the fruit juice are used as a peel and a squeezed refuse. The peel and the squeezed refuse can be used as such. It is preferable that these are cut and pulverized.

The extraction is conducted at from room temperature to elevated temperatures (from 40 to 100° C.) while being allowed to stand or stirred. It can also be conducted under increased pressure. In the extraction, water, alcohol, glycerol and glacial acetic acid are used as a polar solvent as required. These solvents may be used either singly or in combination. Further, water which is brought into direct contact with a peel, such as water used in feeding a fruit or a peel or washing water used in a squeezer may be utilized as an extract. That is, the feeding water and the washing water are satisfactorily contacted with a flesh, a peel and a squeezed residue, and eriocitrin has been already extracted therefrom. Accordingly, they are indeed polar solvent extracts of eriocitrin. Therefore, there is no need to extract the feeding water or the like with a polar solvent, and the subsequent treatment with the synthetic adsorption resin can immediately be conducted.

Then, pulps are removed through centrifugation or membrane separation, and the residue is applied to a synthetic adsorption resin to once adsorb eriocitrin and the like on the resin. As the synthetic adsorption resin, a styrene type and an acrylic type are common, and both are available. Examples thereof include DUOLITE S-861, DUOLITEES-865, AMBERLITEXAD-4, AMBERLITE XAD-7, AMBERLITE XAD-16 (products of Rohm and Haas Co.), DIAION HP 20 and SEPABEADS SP207 (products of Mitsubishi Chemical Industries Ltd.).

Further, high-speed centrifugation or flannel filtration is conducted before passing the extract through the synthetic adsorption resin to remove essential oil ingredients in the extract, making it possible to increase the amount of eriocitrin adsorbed on the resin and further to obtain a food material having a high concentration of eriocitrin efficiently. When the extract is treated with activated carbon instead of the treatment through the high-speed centrifugation or the flannel filtration, the bitter and rough tastes can be removed, and a food material having a high concentration of eriocitrin and having a less bitter taste can be obtained. However, there is also a demerit that the main ingredient is adsorbed on the activated carbon owing to the properties of the activated carbon to decrease the yield of eriocitrin.

After the extract is adsorbed on the resin, it is washed with water or hot water, and crude ingredients containing eriocitrin are eluted with an organic solvent. Then, the solvent is completely removed.

When the resin is washed with water, water of room temperature can be used. However, with the use of hot water of from 40° C. to 100° C., a food material containing eriocitrin and more free from bitter and rough tastes can be produced. Especially, with the use of hot water of from 60° C. to 80° C., a food material containing eriocitrin and all the more free from bitter and rough tastes can be produced. In view of the findings, namely, the property of the synthetic adsorption resin that the higher the temperature of washing water of the resin, the weaker the adsorption force on the resin and the property of the ingredient having the bitter taste that its adsorption force is weaker than that of eriocitrin, it has been clarified that the use of hot water of from 40° C. to 100° C. is preferable.

As the eluent used to recover eriocitrin adsorbed on the resin, an organic solvent is preferable, examples thereof being alcohol, acetone, hexane and chloroform. A polar solvent is especially preferable. Examples thereof include water, alcohol, glycerol and glacial acetic acid. These may be used either singly or in combination. With respect to the condition of the solvent used at this time, when the organic solvent is used as such, ingredients of bitter and rough tastes adsorbed on the resin along with eriocitrin, such as limonin, are also eluted. Therefore, when the solvent is used upon reducing the concentration thereof, the ingredients of bitter and rough tastes are adsorbed on the resin as such, and retained thereon, and eriocitrin alone is eluted selectively. The inventors have discovered this fact for the first time.

As the solvent, alcohol is preferably used. Ethanol is preferable because it is easy to use, and hydrous ethanol is especially preferable. The higher the alcohol content, the higher the eriocitrin content. Accordingly, with respect to the solvent condition, the alcohol content is preferably from 5% to less than 40%. When the ethanol content exceeds 40%, the material having a high concentration of eriocitrin is obtained, but a bitter taste is strong. Thus, a desired food material having a high concentration of eriocitrin with bitter and rough tastes reduced cannot be obtained. Thus, the content of less than 40% is preferable. Further, in order to obtain the desired product efficiently, it is advisable that the ethanol content is between 20 and 30%.

The solvent can be removed by a usual method such as concentration under reduced pressure as required.

The thus-obtained product having the high concentration of eriocitrin can be used, as such, as a food material. The form thereof is not limited to a liquid. It may be used in a food as a treated product such as a paste, a solid, a powder or a diluted product. Solidification and pulverization can be conducted through vacuum drying or freeze-drying as required.

The thus-obtained food material having the high concentration of eriocitrin can be utilized in beverages, foods and alcohols described below.

(1) Soft drinks black tea, barley water, green tea, oolong tea, blend tea, wild grass tea, herb tea, coffee, fruit juice, vegetable drink, cocoa, soybean milk, sports drink, carbonated drink, and milk drink (2) Health foods vitamin drink, nutrient and nutrient aid food (3) Other foods seasonings, vinegar, dressing, soup and "furikake" (foods for sprinkling on cooked rice)

(4) Alcohols cocktail, "chuhai" ("shochu" (low-class distilled spirit) diluted with soda water), "sour" (mixture of spirit, lemon juice, sugar, etc.), beer and wine (5) Sweets candy., biscuit, caramel and snack sweet

EXAMPLE 1

A food material containing eriocitrin was produced as follows using a squeezed residue of lemon as a starting material.

Two-hundred grams of a squeezed residue obtained with an FMC squeezer were pulverized, and 1 liter of water was added thereto. The powder was dipped therein at room temperature for 30 minutes, and the extract was then filtered to obtain a filtrate. This filtrate was centrifuged at 9,000 rpm for 20 minutes, and the supernatant was passed through a synthetic adsorption resin (20 ml: AMBERLITE XAD-16: a product of Rohm & Haas Co.). Then, 100 ml of water (18° C.) were passed, and the product was eluted with 100 ml of ethanol having a concentration of from 10% to 100%. The elute was concentrated under reduced pressure, and the eriocitrin content in the resulting concentrate was measured through high-performance liquid chromatography. This concentrate was dissolved in water, and the flavor thereof was identified through organoleptic evaluation. The results are shown in Table 1.

TABLE 1

| | Eriocitrin content (g) | Recovery (%) | Organoleptic evaluation |
|---|---|---|---|
| water (0% ethanol) | 0.014 | 3.4 | good |
| 5% ethanol | 0.036 | 9.0 | good |
| 10% ethanol | 0.055 | 13.8 | good |
| 20% ethanol | 0.145 | 36.2 | good |
| 30% ethanol | 0.279 | 69.8 | good |
| 40% ethanol | 0.376 | 94.0 | slightly bitter |
| 70% ethanol | 0.388 | 96.8 | bitter |
| 100% ethanol | 0.401 | 100.0 | bitter |

Thus, it was identified that the elution with an aqueous solution having the ethanol content of 30% could provide a food material having a high concentration (40 mg/10 ml) of eriocitrin and having a less bitter taste.

EXAMPLE 2

A food material containing eriocitrin was produced as follows using a peel of lemon as a starting material.

Two kilograms of a lemon peel were pulverized, and 10 liters of water were added thereto. The powder was dipped therein at room temperature for 30 minutes. Then, the extract was filtered to obtain a filtrate. This filtrate was centrifuged at 9,000 rpm for 20 minutes, and the supernatant was passed through a synthetic adsorption resin (500 ml: AMBERLITE XAD-16: a product of Rohm & Haas Co.). Then, 1 liter of water was passed, and 2 liters of hot water of 60° C. and 80 ° C. were passed on the resin. Thereafter, the product was eluted with 1 liter of 30% ethanol. This elute was concentrated under reduced pressure, and the concentrate was dissolved in 10 ml of water. The eriocitrin content in the resulting concentrate was measured through high-performance liquid chromatography, and the flavor was identified through organoleptic evaluation. The results are shown in Table 2.

TABLE 2

| | Eriocitrin content (g) | Organoleptic evaluation |
|---|---|---|
| water (20° C.), then 30% ethanol | 3.07 | good |
| 60° C. hot water, then 30% ethanol | 3.07 | very good |
| 80° C. hot water, then 30% ethanol | 2.93 | very good |

In this manner, it was identified that after the extract of the peel was adsorbed on the synthetic adsorption resin, hot water was first passed, and the product was then eluted with the polar solvent, whereby the bitter and rough tastes could efficiently be removed while maintaining almost the same level of the eriocitrin content.

EXAMPLE 3

Water was added to 100 g of the freeze-dried powder of the concentrate obtained in Example 1, 150 g of sugar, 15 g of honey, 1 g of ascorbic acid, 0.5 g of citric acid and an appropriate amount of a flavor to adjust the amount to 1 kg. The mixture was sterilized at 95° C. for 20 minutes, and 100 ml of the resulting product was sterilely filled in each bottle to produce a health drink.

EFFECTS OF THE INVENTION

According to the invention, a food material having a high concentration of eriocitrin as an antioxidant ingredient derived from citrus fruits can industrially be produced at a low cost. Further, the product obtained by this process is a food material having a high concentration of eriocitrin and having less bitter and rough tastes. Accordingly, when this material is added to beverages or foods, beverages or foods having less unpleasant bitter and rough tastes and having a high antioxidant effect can be obtained. Consequently, foods which help prevent diseases derived from habits of daily life can be provided.

Eriocitrin is an ingredient derived from natural products, and it is contained in a juice of citrus fruits such as lemon and lime which have been already eaten in a large amount of several tens of milligrams per 100 ml. There is no problem with a safety to humans. It is negative in the mutagenicity test according to Rec-assay or Ames assay. Thus, the safety has been identified.

Further, a peel and a squeezed residue are secondary products provided in squeezing a fruit juice. The extraction of an active ingredient by reusing these portions is an invention which is industrially quite useful, and this is extremely profitable from the aspect of utilizing a waste. Still further, in the industry of the fruit juice, besides the peel and the like, waste liquors such as feeding water and washing water used in that treatment are provided in large amounts, and these can be utilized as eriocitrin solutions. In this respect as well, the invention is excellent.

What is claimed is:

1. A process for producing a food material having a high content of eriocitrin, which comprises (1) subjecting at least one member selected from the group consisting of citrus juice, citrus peels, and citrus residue obtained when squeezing juice from citrus fruits, to extraction using a polar solvent;

(2) filtrating the extract solution obtained in step (1) to remove pulp therefrom;

(3) applying the resultant extract solution to a synthetic adsorption resin to adsorb eriocitrin thereon;

(4) washing the resultant synthetic adsorption resin with water having a temperature of 40 to 100° C.;

(5) obtaining eluate containing eriocitrin from the washed synthetic adsorption resin by using, as an eluent, an aqueous ethanol solution having an ethanol concentration in the range of from at least 5% to less than 40%; and (6) removing the ethanol from the obtained eluate containing eriocitrin.

2. The process according to claim 1, wherein the polar solvent in step (1) is water.

3. The process according to claim 1, wherein the removing of the organic solvent is carried out by concentrating the obtained eluate under reduced pressure.

4. The process according to claim 1, wherein the water in step (4) has a temperature of 60 to 80° C.

5. The process according to claim 1, wherein the ethanol concentration is in the range of 20% to 30%.

6. The process according to claim 1, wherein the eluate obtained in step (5) or the resultant eluate obtained in step (6) is subjected to at least one treatment selected from the group consisting of concentrating, forming of paste, drying, and diluting.

7. The process according to claim 1, wherein high-speed centrifugation or flannel filtration to remove essential oil is, further, carried out after step (2) prior to step (3).

8. A process for producing a food material having a high content of eriocitrin, which comprises (1) obtaining a water used to feed or wash at least one member selected from the group consisting of citrus fruits, citrus fleshes, citrus peels, and citrus residue obtained when squeezing juice from citrus fruits;

(2) removing pulp from the water obtained in step (1);

(3) applying the resultant water to a synthetic adsorption resin to adsorb eriocitrin thereon;

(4) washing the resultant synthetic adsorption resin with water having a temperature of 40 to 100° C.;

(5) obtaining eluate containing eriocitrin from the washed synthetic adsorption resin by using, as an eluent, an aqueous ethanol solution having an ethanol concentration in the range of from at least 5% to less than 40%; and (6) removing the ethanol from the obtained eluate containing eriocitrin.

9. The process according to claim 8, wherein the removing of the organic solvent is carried out by concentrating the obtained eluate under reduced pressure.

10. The process according to claim 8, wherein the water in step (4) has a temperature of 60 to 80°C.

11. The process according to claim 8, wherein the ethanol concentration is in the range of 20% to 30%.

12. The process according to claim 8, wherein the eluate obtained in step (5) or the resultant eluate obtained in step (6) is subjected to at least one treatment selected from the group consisting of concentrating, forming of paste, drying, and diluting.

13. The process according to claim 8, wherein high-speed centrifugation or flannel filtration to remove essential oil is, further, carried out after step (2) prior-to step (3).

* * * * *